United States Patent
Kim

(10) Patent No.: US 11,999,803 B2
(45) Date of Patent: *Jun. 4, 2024

(54) PROTEASOME INHIBITORS

(71) Applicant: University of Kentucky Research Foundation, Lexington, KY (US)

(72) Inventor: Kyung Bo Kim, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/169,158

(22) Filed: Feb. 14, 2023

(65) Prior Publication Data

US 2023/0357319 A1 Nov. 9, 2023

Related U.S. Application Data

(62) Division of application No. 17/265,344, filed as application No. PCT/US2019/045350 on Aug. 6, 2019, now Pat. No. 11,578,101.

(60) Provisional application No. 62/715,149, filed on Aug. 6, 2018.

(51) Int. Cl.
*A61P 25/28* (2006.01)
*C07K 5/12* (2006.01)

(52) U.S. Cl.
CPC .............. *C07K 5/123* (2013.01); *A61P 25/28* (2018.01); *C07K 5/126* (2013.01)

(58) Field of Classification Search
CPC ...... C07K 5/123; C07K 5/126; C07K 5/0823; C07K 5/1008; C07K 5/06165; A61P 25/28; A61P 35/00; C07D 498/04; C07D 498/08; A61K 38/00
See application file for complete search history.

(56) References Cited

U.S. PATENT DOCUMENTS

| | | | |
|---|---|---|---|
| 11,578,101 B2* | 2/2023 | Kim | ................ C07K 5/06165 |
| 2008/0064659 A1 | 3/2008 | Kim et al. | |
| 2014/0255300 A1 | 9/2014 | Bachovchin | |
| 2015/0299250 A1 | 10/2015 | Abell et al. | |

FOREIGN PATENT DOCUMENTS

| | | |
|---|---|---|
| CN | 108191957 A | 3/2018 |
| CN | 108117582 A | 6/2018 |
| WO | WO2013033396 A2 | 3/2013 |
| WO | WO2014/152134 A1 | 9/2014 |

OTHER PUBLICATIONS

Kaarniranta, Ket al., NF-kappaB signaling as a putative target for omega-3 metabolites in the prevention of age-related macular degeneration (AMD), Experimental Gerontology 44(11), pp. 685-688, 2009.
Seo, EJ et al., Phytochemicals as Inhibitors of NF-κB for treatment of Alzheimer's disease, Pharmacological Research 129, pp. 262-273, Mar. 2018.
Srinivasan, Met al., Significance of NF-κB as a pivotal therapeutic target in the neurodegenerative pathologles of Alzheimer's disease and multiple sclerosis, Expert Opinion on Therapeutic Targets 19(4), pp. 1-27 (pp. 471-487), 2015.
Li, ZW et al., NF-kappaB 1l1 the pathogenesis and treatment of multiple myeloma, Current Opinion in Hematology 15 (4), p. !3 391-399, 2008.
Eva Ogorevc et al: "A patent review of immunoproteasome inhibitors", Expert Opinion on Therapeutic Patents, vol. 28, No. 7, Jun. 14, 2018, pp. 517-540.
Lee Min Jae et al: "Macrocyclic Immunoproteasome Inhibitors as a Potential Therapy for Alzheimer's Disease", Journal of Medicinal Chemistry, vol. 64, No. 15, Aug. 12, 2021, pp. 10934-10950.
Krahn et al (Curr. Med.Chem., 2011, 18(33), 5052-60) (Year: 2011).
Patani et al (Chem.Rev., 1996, 96, 3147-3176) (Year: 1996).

* cited by examiner

*Primary Examiner* — Sudhakar Katakam
(74) *Attorney, Agent, or Firm* — Stites & Harbison PLLC; Mandy Wilson Decker

(57) ABSTRACT

Unique compounds useful for inhibiting a proteasome in a cell, pharmaceutical compositions and methods of their use are provided herein.

2 Claims, 4 Drawing Sheets

PROTEASOME INHIBITORS

RELATED APPLICATIONS

This application is a division of U.S. Pat. No. 11,578,101, which issued from a U.S. national stage entry of International Patent Application No. PCT/US2019/045350 filed Aug. 6, 2019, which claims priority from U.S. Provisional Application Ser. No. 62/715,149 filed Aug. 6, 2018, the entire disclosure of which is incorporated herein by this reference.

GOVERNMENT INTEREST

This invention was made with government support under RO1 CA188354 awarded by National Institutes of Health. The government has certain rights in the invention.

TECHNICAL FIELD

The presently-disclosed subject matter relates to unique peptide epoxyketones, their pharmaceutically acceptable salts, process(es) for their preparation, pharmaceutical compositions containing the unique proteasome inhibitors, and methods of treating disease(s) in a subject, including cancer, via administration of the peptide epoxyketones.

INTRODUCTION

The proteasome is a key player in one of the most fundamental processes in eukaryotic cells, the ubiquitin-dependent protein degradation pathway. The proteasome is a large multi-subunit protease that degrades the majority of cellular proteins. The proteasome also controls critical cellular process, such as the cell cycle, via the regulated degradation of signaling proteins. By perturbing these processes, inhibition of the proteasome leads to apoptosis, especially in cancer cells. It is for this reason that proteasome inhibitors have become critically important therapies in the treatment of multiple myeloma.

Although the distinct catalytic subunits of the different proteasome isoforms have been suggested to play roles in adding antigenic diversity to peptides generated from protein degradation, the catalytic subunits responsible for the CT-L activity (β5 and β5i) are thought to be most physiologically important and have been recognized as the key targets of bortezomib (Velcade®), the first-in-class proteasome inhibitor approved by the FDA in 2003 for the treatment of relapsed multiple myeloma (MM), and carfilzomib, a second-generation proteasome inhibitor approved by the FDA for the treatment of relapsed multiple myeloma patients who have received at least two prior therapies, including bortezomib. The addition of these proteasome inhibitors to chemotherapeutic armaments has dramatically improved the therapeutic landscape for patients with multiple myeloma (MM). Despite the remarkable successes of these drugs in the clinic, intrinsic and acquired drug resistance remains a major clinical challenge. Additionally, these drugs have failed to provide clinical benefit to patients with solid cancers, further adding to the need for next generation proteasome inhibitors.

Alzheimer's disease (AD) is the most common form of dementia and poses a great health-care challenge of the 21st century as aging population continues to grow. Intensive research efforts have been put forth for more than three decades, yet little is known about the cause of AD. The discoveries of amyloid β (Aβ) and tau, the main components of plaques and tangles respectively, decades ago has provided great hope for disease-modifying drugs, but yet there are no curative treatments. Currently, available drugs for the AD are only symptomatic ones, which are effective for a limited time without altering the course of disease progress. The extracellular plaque deposits of the β-amyloid peptide (Aβ) and the neurofibrillary tangles of the microtubule binding protein tau inside neuron are widely considered as two major pathological hallmarks required for a diagnosis of AD. So far, clinical trials to test promising new treatments aimed at amyloid β(Aβ) and tau protein using monoclonal antibodies and small molecules have yielded disappointing results (clinical trials, Merck & Lily, 2016, 2017 and LMTM by TauRx, 2016). For example, a number of large-scale clinical trials have been performed to evaluate new treatments aimed at soluble Aβ as well as insoluble aggregates, but the results have been disappointing so far.[1,2] Similarly, tau-directed drug development approach has yet to yield promising therapeutics.[3,4] As a result, alternative processes not directly connected to Aβ or tau pathways have been of substantial interest to researchers. For example, interest has been growing in other targets such as components of innate inflammatory pathways.

In response to cellular stress or pro-inflammatory cytokines such as TNF-α or interferon (INF)-γ, cells upregulate variant forms of proteasome catalytic subunits, known as immuno-subunits. As a result, cells undergo dynamic changes in proteasome assembly to form the immunoproteasome (iP), which harbors immuno-subunits LMP7, LMP2 and Mecl-1 instead of constitutive counterparts X, Y and Z, respectively. It has been reported that overall activity of the iP is considerably enhanced compared to the constitutive proteasome (cP)[5] and that shaping the antigenic repertoire of MHC class I is a major function of the iP.[6] The iP was also shown to be vital for the degradation of misfolded and oxidant-damaged proteins to prevent disease progress.[5,7] A selective inhibitor of LMP7 is shown to block cytokine production and attenuate progression of experimental arthritis in mouse models,[8] implicating an important role of LMP7 during inflammation. Although the cellular functions of other immuno-subunits, LMP2 and Mecl-1, are not actively investigated so far, recent studies report that LMP2 has no role in pro-inflammatory cytokine production or NF-kB activation in cancer cells and human peripheral blood mononuclear cells.[9,10]

The proteasome appears to play a role in the pathogenesis of neurodegenerative diseases such as AD. Several previous studies reported significant alterations in proteasome activity and accumulation of ubiquitinated protein deposits in the brains and cerebrospinal fluid of AD patients and in rodent models of disease.[11-14] In in vitro studies, Aβ peptides have been shown to reduce the activity of 20S proteasomes, while increasing activity of the 20S proteasomes capped with the 19S and/or 11S regulators. Accumulation of insoluble tau is also shown to be associated with a decrease in the catalytic activity of brain 26S proteasomes and higher levels of ubiquitinated proteins.[15] On the other hand, other researchers reported rather disparate observations that elevated IP expression and activity is positively correlate with increasing severity of tau pathology and microglial activation in AD patients as well as in a mouse model of brain injury.[16-19] Similarly, elevated expression of iP was spotted in microglia and astrocytes surrounding Aβ plaques isolated from AD animals.[20] In a mouse model of Aβ deposition, LMP7 knockout resulted in alterations in microglial cytokine production profile and improved cognitive deficits,[21] indicating a role of LMP7 subunit in Aβ-induced neuroinflammation.

While the LMP7, which is responsible for CT-L activity, has drawn considerable interest as a potential therapeutic target for inflammatory diseases, LMP2, which also cleaves after hydrophobic amino acid residues, is not considered a therapeutic target. It has been suggested that the contribution of LMP2 to overall CT-L activity of iP is relatively small compared to that of LMP7.[22] This was further supported by recent studies showing ineffectiveness of LMP2-selective inhibitors on inhibition of cytokine production.[3] For this reason, LMP2 has not been actively pursued as a therapeutic target in autoimmune diseases. Regarding the role of LMP2 in neurodegenerative diseases, there have so far been very few studies conducted, reporting moderate up-regulation of LMP2 expression in AD patients.[18,23]

There is still much work to be done to provide proteasome inhibitors which overcome intrinsic and acquired drug resistance, which have clinical utility outside of multiple myeloma, and which have improved pharmacokinetic properties.

Accordingly, the subject matter of the present disclosure relates to the development of unique proteasome inhibitors that have improved pharmacokinetic properties and broader and/or unique treatment applications as compared to compounds known in the art.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter further includes a pharmaceutical composition, which includes at least one compound according to formula (I), formula (II), formula (III) and formula (IV), and a pharmaceutically-acceptable carrier.

The presently-disclosed subject matter also includes a method of inhibiting a proteasome in a cell, which involves administering or contacting the compound of formula (I), formula (II), formula (III) and formula (IV) to the cell. In some embodiments, the compound is administered as a general proteasome inhibitor. In some embodiments, a compound is administered as an immunoproteasome subunit LMP2 inhibitor.

In some embodiments, the unique proteasome inhibitor is a compound of formula (I), a pharmaceutically acceptable salt, solvate, or physiologically functional derivative thereof:

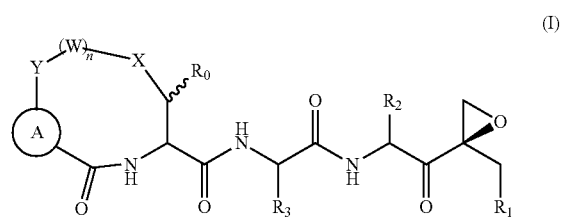

In some embodiments, the unique proteasome inhibitor is a compound of formula (II), a pharmaceutically acceptable salt, solvate, or physiologically functional derivative thereof:

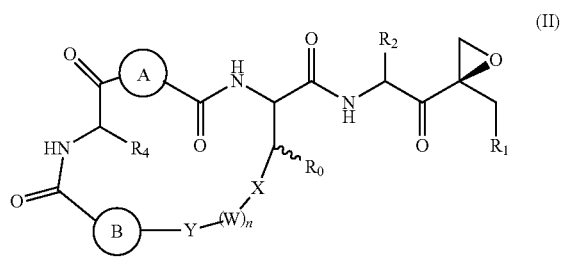

In some embodiments, the unique proteasome inhibitor is a compound of formula (III), a pharmaceutically acceptable salt, solvate, or physiologically functional derivative thereof:

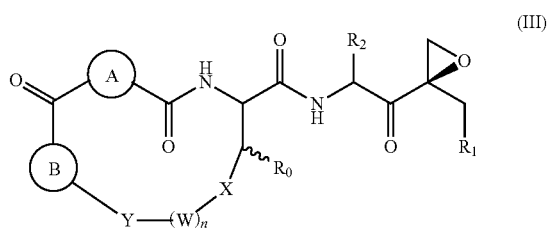

In some embodiments, the unique proteasome inhibitor is a compound of formula (IV), a pharmaceutically acceptable salt, solvate, or physiologically functional derivative thereof:

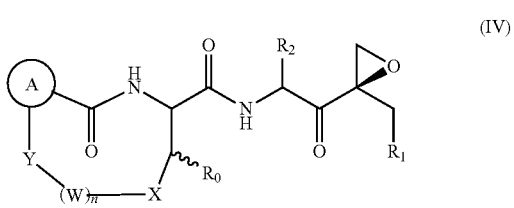

The presently-disclosed subject matter also includes a method of treating a disease in a subject, which includes administering an effective amount of a pharmaceutical composition containing the compound of formula (I), formula (II), formula (III) and formula (IV) to the subject. The disease can be, for example, a neurodegenerative disease, an autoimmune disease, or cancer. In some embodiments, the disease is Alzheimer's disease (AD), age-related macular degeneration (AMD), or multiple myeloma (MM). In some embodiments, the administering results in improved memory function. In some embodiments, the disease is relapsed/refractory MM and/or is resistant to carflizomib and/or bortezomib.

In some embodiments, the administering is to a cell, in some instances the cell is a cancer cell or a retinal pigment epithelial cell. In other instances, the administering is to a subject.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1A:
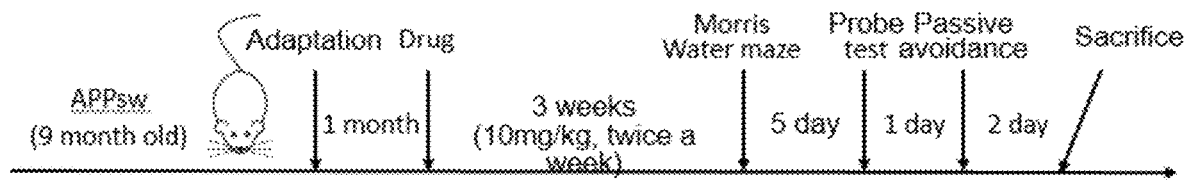
FIGS. 1A-1D illustrates amelioration of cognitive deficits in APPsw (Tg2576) mice treated with YU102, a selective LMP2 inhibitor, and YU102 epi, a stereoisomer of YU102 that does not inhibit LMP2.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes inhibitors of the 20S proteasome, including a series of proteasome-inhibiting peptide epoxyketones as disclosed herein. With reference to the following Formula V, the compounds disclosed herein, unlike previously-known proteasome-inhibiting peptide epoxyketones, include macrocyclic peptides connecting the $R_4$ to neighboring $R_5$ or $R_6$ residues, or macrocyclic peptides connecting the $R_3$ residues to $R_4$ or $R_5$ or $R_6$ residues, or macrocyclic peptides linking the $R_3$ to $R_4$ proline or $R_4$ proline mimic residues.

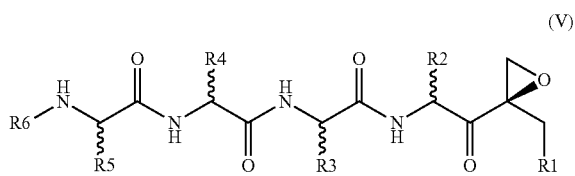

(V)

As disclosed herein, macrocyclic peptides containing peptide epoxyketone pharmacophore can selectively target immunoproteasome LMP2 and/or LMP7 subunits, inhibition of which displays efficacy against in vivo Alzheimer's Disease (AD) and age-related macular degeneration (AMD) models.

The presently disclosed subject matter includes a unique proteasome inhibitor, including a compound of formula (I), (II), (III), or (IV), or a pharmaceutically acceptable salt, solvate, or physiologically functional derivative thereof.

In some embodiments, the compound is a proteasome subunit LMP2 inhibitor or a general proteasome inhibitor. In some embodiments, the unique proteasome inhibitor is a compound of formula (I), a pharmaceutically acceptable salt, solvate, or physiologically functional derivative thereof:

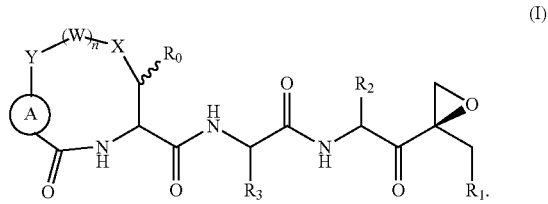

(I)

In some embodiments, the unique proteasome inhibitor is a compound of formula (II), a pharmaceutically acceptable salt, solvate, or physiologically functional derivative thereof:

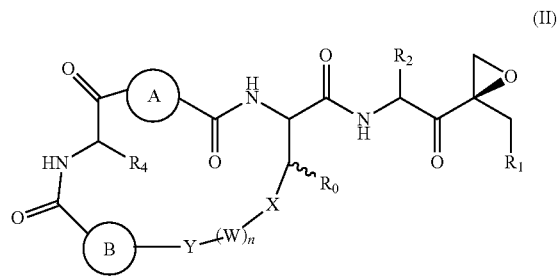

(II)

In some embodiments, the unique proteasome inhibitor is a compound of formula (III), a pharmaceutically acceptable salt, solvate, or physiologically functional derivative thereof:

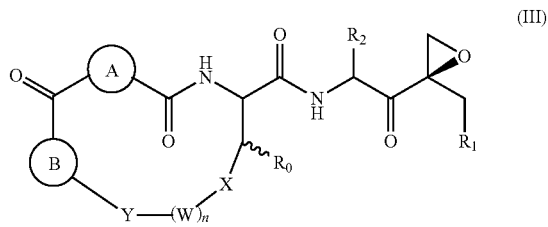

(III)

In some embodiments, the unique proteasome inhibitor is a compound of formula (IV), a pharmaceutically acceptable salt, solvate, or physiologically functional derivative thereof:

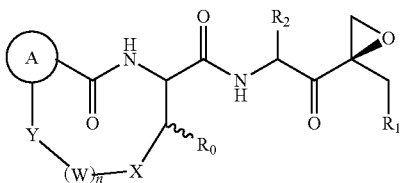
(IV)

In some embodiments of a compound of Formulae (I), (II), (III), and (IV), X and Y are independently selected from the group consisting of —CH$_2$—, —CH$_2$CH$_2$—, —O—, —CH$_2$O—, —NH—, —CH$_2$NH—, —N(CH$_3$)—, —CH$_2$N(CH$_3$)—, —C(=O)—, —CH$_2$C(=O)—, —C$_6$H$_4$—, —CH$_2$—(C$_6$H$_4$)—, —(C$_6$H$_4$)-F$_{1-4}$-, —CH$_2$—C$_6$H$_4$-F$_{1-4}$-, -pyrazole-, -imidazole-, -thiazole-, -oxazole-, -morpholine-, -pyridine-, -piperazine-, and -pyrrole-.

In some embodiments of a compound of formulae (I), (II), (III), and (IV), W is selected from the group consisting of —CH$_2$—, —CH$_2$OCH$_2$—, —CH$_2$CH$_2$O—, and —CH$_2$CH$_2$OCH$_2$CH$_2$—.

In some embodiments of a compound of formulae (I), (II), (III), and (IV), n is 1, 2, 3, 4, 5, 6, 7, or 8.

In some embodiments of a compound of formulae (I), (II), (III), and (IV), R$_0$ is selected from the group consisting of H, OH, F, CH$_3$, and OCH$_3$.

In some embodiments of a compound of formulae (I), (II), (III), and (IV), R$_1$ is

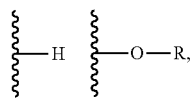

wherein R is H, CH$_3$, isopropyl, t-butyl, methoxymethyl (MOM), menthoxyethoxy methyl (MEM), or (CH$_2$)nCH$_3$ wherein n is 1, 2, or 3.

In some embodiments of a compound of formulae (I), (II), (III), and (IV), R$_1$ is

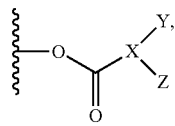

wherein X, Y, and Z are independently selected from the group consisting of H, CH, N, CH$_3$, and CH$_2$CH$_3$.

In some embodiments of a compound of formulae (I), (II), (III), and (IV), R$_1$ is

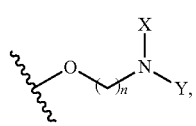

wherein X and Y are independently selected from the group consisting of H, CH$_3$, and (CH$_2$)nCH$_3$ wherein n is 1, 2, or 3.

In some embodiments of a compound of formulae (I), (II), (III), and (IV), R$_1$ is

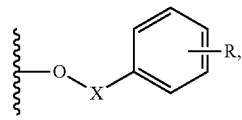

wherein X is CH$_2$ or C=O; and R is H, CH$_3$, N(CH$_3$)$_2$, or Fn, wherein n is 0, 1, 2, 3, 4, or 5.

In some embodiments of a compound of formulae (I), (II), (III), and (IV), R$_1$ is

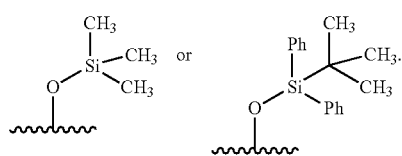

In some embodiments of a compound of formulae (I), (II), (III), and (IV), R$_1$ is

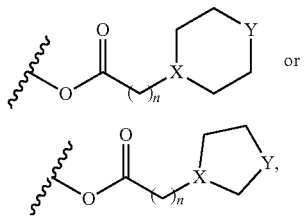

wherein X is CH or N; Y is CH$_2$, O, or N-R, wherein R is H, CH$_3$ or COCH$_3$; and n is 0, 1, or 2.

In some embodiments of a compound of formulae (I), (II), (III), and (IV), R$_1$ is

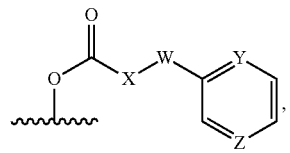

wherein X, Y, and Z are independently selected from the group consisting of CH, CH$_2$, N, NH, and O; and W is CH$_2$ or CH$_2$CH$_2$.

In some embodiments of a compound of formulae (I), (II), (III), and (IV), R$_1$ is

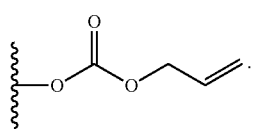 [SMILES: *OC(=O)OCC=C]

In some embodiments of a compound of formulae (I), (II), (III), and (IV), $R_1$ is

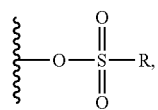

wherein R is $CH_3$, $CH_2CH_2Ph\text{-}Fn$, or $CH_2PhFn$, wherein n is 0, 1, 2, 3, 4, or 5.

In some embodiments of a compound of formulae (I), (II), (III), and (IV), $R_1$ is

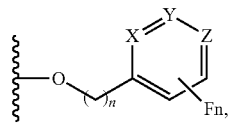

wherein X, Y, and Z are independently selected from N and CH, and n is 0, 1, 2, or 3.

In some embodiments of a compound of formulae (I), (II), (III) and (IV), $R_2$, $R_3$ and/or $R_4$ can each be Gly, Ala, Pro, Leu, Ile, Phe, Tyr, Val, Ser, methyloxySerine, homoPhe, norVal, or norLeu.

In some embodiments of a compound of formulae (I), (II), (III) and (IV), $R_2$, $R_3$ and/or $R_4$ can each be

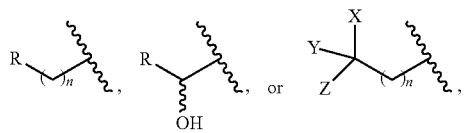

wherein X and Y are independently selected from the group consisting of H, $CH_3$, and $CH_2CH_3$; R and Z are independently selected from the group consisting of H, OH, $OCH_3$, $OCH_2CH_3$, Ph, and OPh; and n is 1, 2, or 3.

In some embodiments of a compound of formulae (I), (II), (III) and (IV), $R_2$, $R_3$ and/or $R_4$ can each be

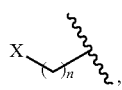

wherein X is cyclopropyl, cyclopentyl, or cyclohexyl, and n is 1, 2, or 3.

In some embodiments of a compound of formulae (I), (II), (III) and (IV), $R_2$, $R_3$ and/or $R_4$ can each be

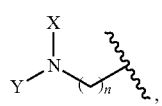

wherein X and Y are independently selected from the group consisting of H, $CH_3$, $CO(CH_3)$, and $CO2Bzl$, and n is 1, 2, or 3.

In some embodiments of a compound of formulae (I), (II), (III) and (IV), $R_2$, $R_3$ and/or $R_4$ can each be

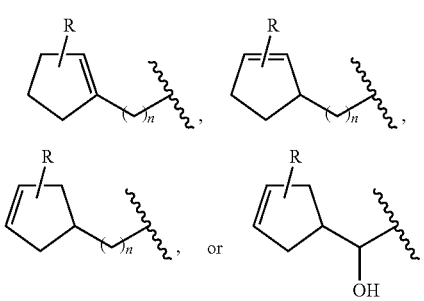

wherein R is H, $CH_3$, or $(F)_{1-3}$, and n is 1, 2, or 3.

In some embodiments of a compound of formulae (I), (II), (III) and (IV), $R_2$, $R_3$ and/or $R_4$ can each be

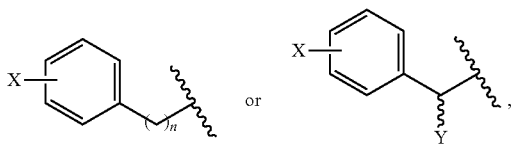

wherein X and Y are independently selected from the group consisting of H, Fn, Cl, $CH_3$, $OCH_3$, OH, $COCH_3$, $NH_2$, $NH(CH_3)$ and NHFmoc, and n is 1, 2, or 3.

In some embodiments of a compound of formulae (I), (II), (III) and (IV), $R_2$, $R_3$ and/or $R_4$ can each be

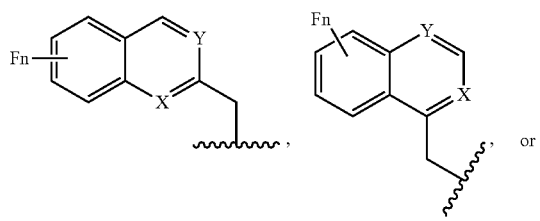

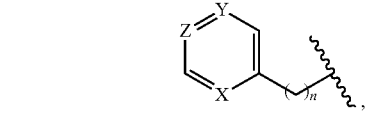

wherein X, Y, and Z are independently selected from CH and N, and n is 1, 2, or 3.

In some embodiments of a compound of formulae (I), (II), (III) and (IV), $R_2$, $R_3$ and/or $R_4$ can each be

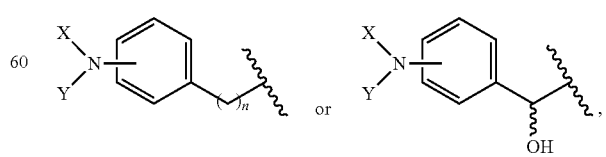

wherein X and Y are independently selected from the group consisting of H, $CH_3$, and $COCH_3$, and n is 1, 2, 3, or 4.

In some embodiments of a compound of formulae (I), (II), (III) and (IV), $R_2$, $R_3$ and/or $R_4$ can each be

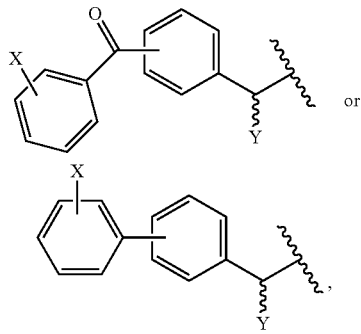 or , wherein X is H, Fn, $CH_3$, or $OCH_3$; Y is H or OH, and n is 1, 2, 3, 4, or 5.

In some embodiments of a compound of formulae (I), (II), (III) and (IV), $R_2$, $R_3$ and/or $R_4$ can each be

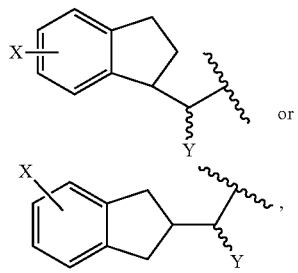 or , wherein X and Y are independently selected from the group consisting of H, Fn, $CH_3$ $OCH_3$, OH, $COCH_3$; and n is 1, 2, 3, 4, or 5.

In some embodiments of a compound of formulae (I), (II), (III) and (IV), $R_2$, $R_3$ and/or $R_4$ can each be

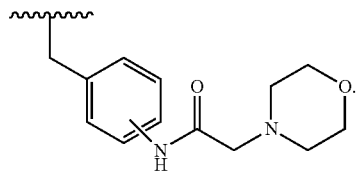

In some embodiments of a compound of formulae (I), (II), (III) and (IV), $R_2$, $R_3$ and/or $R_4$ can each be

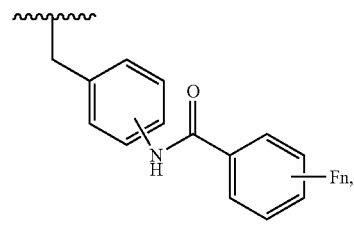

wherein n is 0, 1, 2, 3, 4, or 5.

In some embodiments of a compound of formulae (I), (II), (III) and (IV), $R_2$, $R_3$ and/or $R_4$ can each be

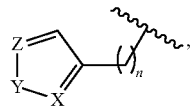, wherein X, Y, and Z are independently selected from the group consisting of CH, $CH_2$, N, NH, $N(CH_3)$, and O, and n is 1, 2, or 3.

In some embodiments of a compound of formulae (I), (II), (III) and (IV), $R_2$, $R_3$ and/or $R_4$ can each be

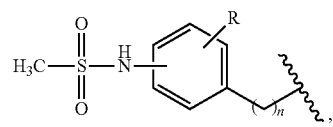, wherein R is H, $CH_3$, or Fn, wherein n is 0, 1, 2, or 3.

In some embodiments of a compound of formulae (I), (II), (III) and (IV), $R_2$, $R_3$ and/or $R_4$ can each be

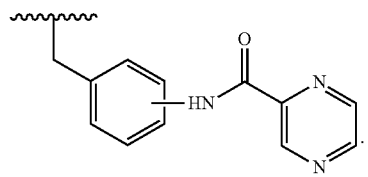.

In some embodiments of a compound of formulae (I), (II), (III) and (IV), $R_2$, $R_3$ and/or $R_4$ can each be

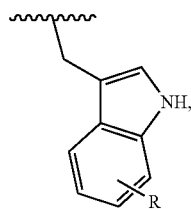

wherein R is H, Fn, or $(CH_3)n$, wherein n is 0, 1, 2, 3, or 4.

In some embodiments of a compound of formulae (I), (II), (III) and (IV), A and B can each be

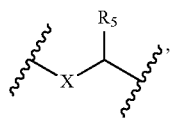, wherein $R_5$ is selected from the group consisting of H, $CH_3$, $(CH_2)_{1-3}CH_3$, $CH(CH_3)_2$, $CH_2CH(CH_3)_2$, $CH(CH_3)CH(CH_3)_2$, $CH_2OH$, $CH_2OCH_3$, $CH_2(C_6H_5)$, $CH_2CH_2(C_6H_5)$, and $CH_2(C_6H_4)$-OH; and X is selected from the group consisting of $CH_2$, NH, and $N(CH_3)$.

In some embodiments of a compound of formulae (I), (II), (III) and (IV), A and B can each be

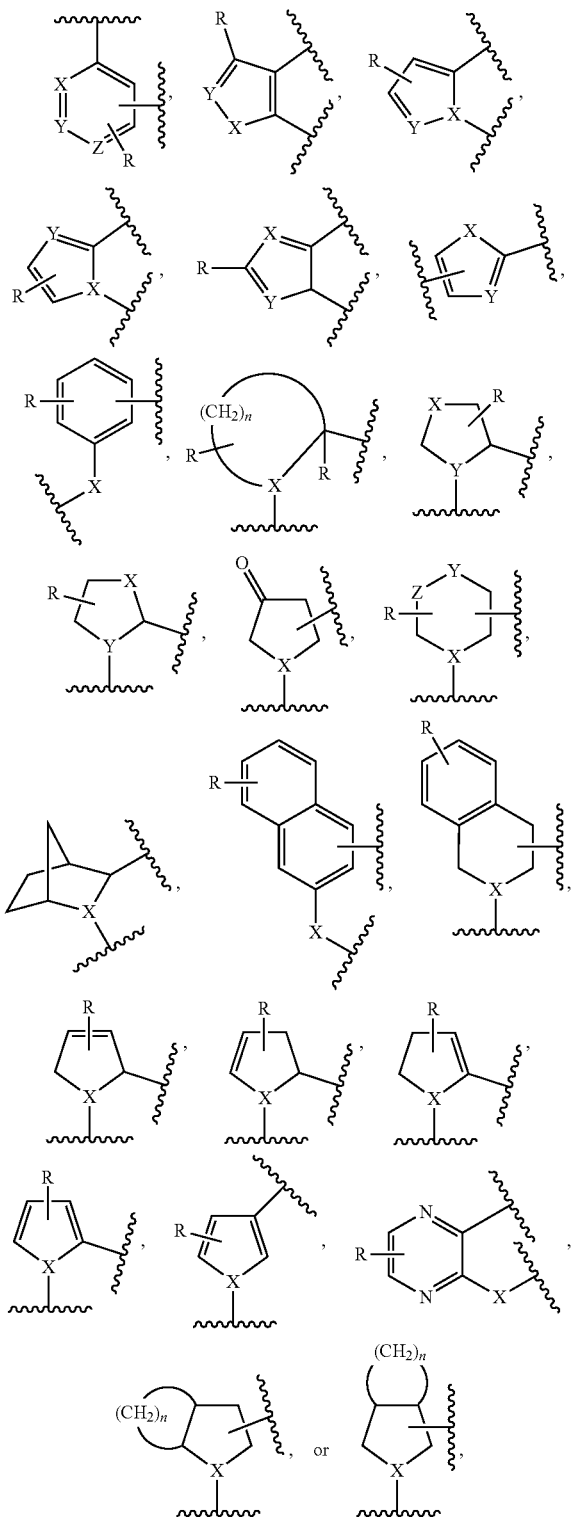

wherein X, Y, and Z are independently selected from the group consisting of CH, $CH_2$, C=O, N, NH, O, S, and N-R'; R' is H, OH, $(F)_{1-4}$, $CH_3$, $OCH_3$, $CH_2OCH_3$, $NH_2$, $NH(CH_3)$, $N(CH_3)_2$, N(C=O)$CH_3$, phenyl, phenyl$(F)_{1-4}$, pyrazole, imidazole, thiazole, oxazole, morpholine, pyridine, piperazine, or pyrrole; and n is 2, 3, 4, or 5.

The presently-disclosed subject matter further includes a pharmaceutical composition, which includes at least one compound according to formula (I), (II), (III) or (IV), and a pharmaceutically-acceptable carrier.

The presently-disclosed subject matter also includes a method of inhibiting a proteasome in a cell, which involves administering or contacting the compound of formula (I), (II), (III) or (IV), to the cell. In some embodiments, the compound is administered as a general proteasome inhibitor. In some embodiments, a compound is administered as an immunoproteasome LMP2 inhibitor. The administering or contacting the compound to the cell can be, for example, a cancer cell. In other embodiments, the administration of contacting the compound to the cell can be to a Retinal Pigment Epithelium (RPE) cell.

The presently-disclosed subject matter also includes a method of treating a disease in a subject, which includes administering an effective amount of a pharmaceutical composition containing the compound of formula (I), (II), (III) or (IV) to the subject. The disease can be, for example, a neurodegenerative disease, an autoimmune disease, or cancer. In some embodiments, the disease is Alzheimer's Disease (AD), age-related macular degeneration (AMD) or Multiple Myeloma (MM). In some embodiments, the disease is relapsed/refractory MM.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one compound provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The term "physiologically functional derivative" means any pharmaceutically acceptable derivative of a compound of the present disclosure. For example, an amide or ester of a compound of formula (I), which upon administration to a subject, particularly a mammal, is capable of providing, either directly or indirectly, a compound of the present disclosure of an active metabolite thereof.

As will be recognized by one of ordinary skill in the art, the terms "suppression," "suppressing," "suppressor," "inhibition," "inhibiting" or "inhibitor" do not refer to a complete elimination of a value in all cases. Rather, the skilled artisan will understand that the term "suppressing" or "inhibiting" refers to a reduction or decrease in a measured value, qualitatively or quantitatively. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments the subject in need thereof will be suffering or will have been diagnosed with one or more neoplastic or hyperproliferative diseases, disorders, pathologies, or conditions. Examples of such diseases, conditions, and the like include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Other cancers include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof.

A subject may also be in need thereof because they have acquired diseases or conditions such as autoimmune diseases such as, but not limited to, Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)).

A subject may also be in need thereof because they have neurodegenerative conditions such as Alzheimer's Disease, amyotrophic lateral sclerosis, Parkinson's, and Huntington's. A subject may also be in need thereof because of conditions such as age-related macular degeneration (AMD).

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

Moreover, the subject matter of the present disclosure relates to the development of unique proteasome inhibitors that utilize a macrocyclic peptide epoxyketone scaffold.

In some embodiments, the unique proteasome inhibitors of the present disclosure comprise a substituted macrocyclic peptide epoxyketone scaffold, which provides for relatively potent inhibition of proteasome.

In some embodiments, the subject matter of the present disclosure is directed to proteasome inhibitors that have improved pharmacokinetic properties and broader treatment applications than those previously known in the art. In some embodiments, the peptide proteasome inhibitors of the present disclosure demonstrate activity against multiple myeloma with acquired resistance to bortezomib and/or carfilzomib, neurodegenerative disease such as AD, and AMD.

Certain compounds of formulae disclosed herein may exist in stereoisomeric forms (e.g., they may contain one or more asymmetric carbon atoms, or they may exhibit cis-trans isomerism), and, the individual stereoisomers and mixtures of these are included within the scope of the present disclosure.

The unique proteasome inhibitors of the present disclosure may be used for the treatment of a disease or condition, such as cancer. In some embodiments, there is provided a pharmaceutical composition for use in the treatment (including prophylaxis) of one or more conditions or indications set forth herein, which comprises a compound of formula (I), (II), (III) or (IV), or a pharmaceutically acceptable salt, solvate, or physiologically functional derivative thereof, and a pharmaceutically acceptable carrier or excipient.

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

Still further, the presently-disclosed subject matter includes a method for treating cancer. In some embodiments the method comprises administering a compound, including one of the compounds described herein, to a subject in need thereof. In some embodied methods a plurality of compounds according the present disclosure are administered simultaneously or in a predetermined sequence.

There are also provided processes for the preparation of a non-peptide proteasome inhibitor according to the present disclosure. For example, in some embodiments, the present disclosure provides processes for the preparation of a compound of formula (I), (II), (III) or (IV), or a pharmaceutically acceptable salt, solvate, or physiologically functional derivative thereof.

Additionally, the present disclosure provides uses of a compound of formula (I), (II), (III) or (IV), or a pharmaceutically acceptable salt, a solvate, or physiological derivative thereof in the preparation or manufacture of a drug and/or medicine, especially a medicine for the treatment of cancer, neurodegenerative disease, or autoimmune disease in a mammal.

In some embodiments, the present disclosure provides methods for treating a subject with neurodegenerative disease, autoimmune disease, or cancer by administering to the subject an effective amount of at least one proteasome inhibitor.

In some embodiments, the presently-disclosed subject matter provides a proteasome inhibitor comprising at least one peptide epoxyketone. In some embodiments, the proteasome inhibitor is an epoxyketone that generally inhibits the proteasome or is selective for LMP2.

In some embodiments, the presently-disclosed subject matter provides a method of inhibiting a proteasome in a cell, which involves administering an effective amount of a compound of formula (I), (II), (III) or (IV) to the cell.

In certain embodiments, the present disclosure provides a method of treating a disease, wherein the method comprises administering to a subject at least one proteasome inhibitor, wherein the proteasome inhibitor comprises at least one peptide epoxyketone.

In certain embodiments, the present disclosure provides a method of treating a disease, wherein the method comprises administering to a subject an effective amount of a pharmaceutical composition containing at least one compound according to formula (I), (II), (III) or (IV).

In some embodiments, the present disclosure is directed to a pharmaceutical composition comprising at least one proteasome inhibitor, wherein the proteasome inhibitor includes at least one peptide epoxyketone.

In some embodiments, the present disclosure is directed to a pharmaceutical composition comprising at least one compound according to formula (I), (II), (III) or (IV).

In some embodiments, the present disclosure teaches a method of synthesizing a proteasome inhibitor comprising at least one peptide epoxyketone and macrocyclic peptide.

Further, the present disclosure provides, in certain embodiments, a method of treating a disease in a subject comprising the administration of an effective amount of a pharmaceutical composition containing a protease inhibitor, a pharmaceutically acceptable salt, solvate or physiologically functional derivative thereof and pharmaceutically acceptable excipient to the subject.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1% from the specified amount, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1: A new class of peptide epoxyketones will be shown to have efficacies against relapsed/refractory multiple myeloma and neurodegenerative diseases such as Alzheimer's disease. Some of presently-disclosed class of inhibitors will show efficacy against patient MM samples that are resistant to FDA-approved proteasome inhibitors bortezomib and carfilzomib. In addition, macrocyclic peptides targeting immunoproteasome catalytic subunits will be shown to have efficacy against in vivo AD models, such as swAPP transgenic mouse models.

Example 2: Synthesis of epoxyketones for Formula II-III compounds

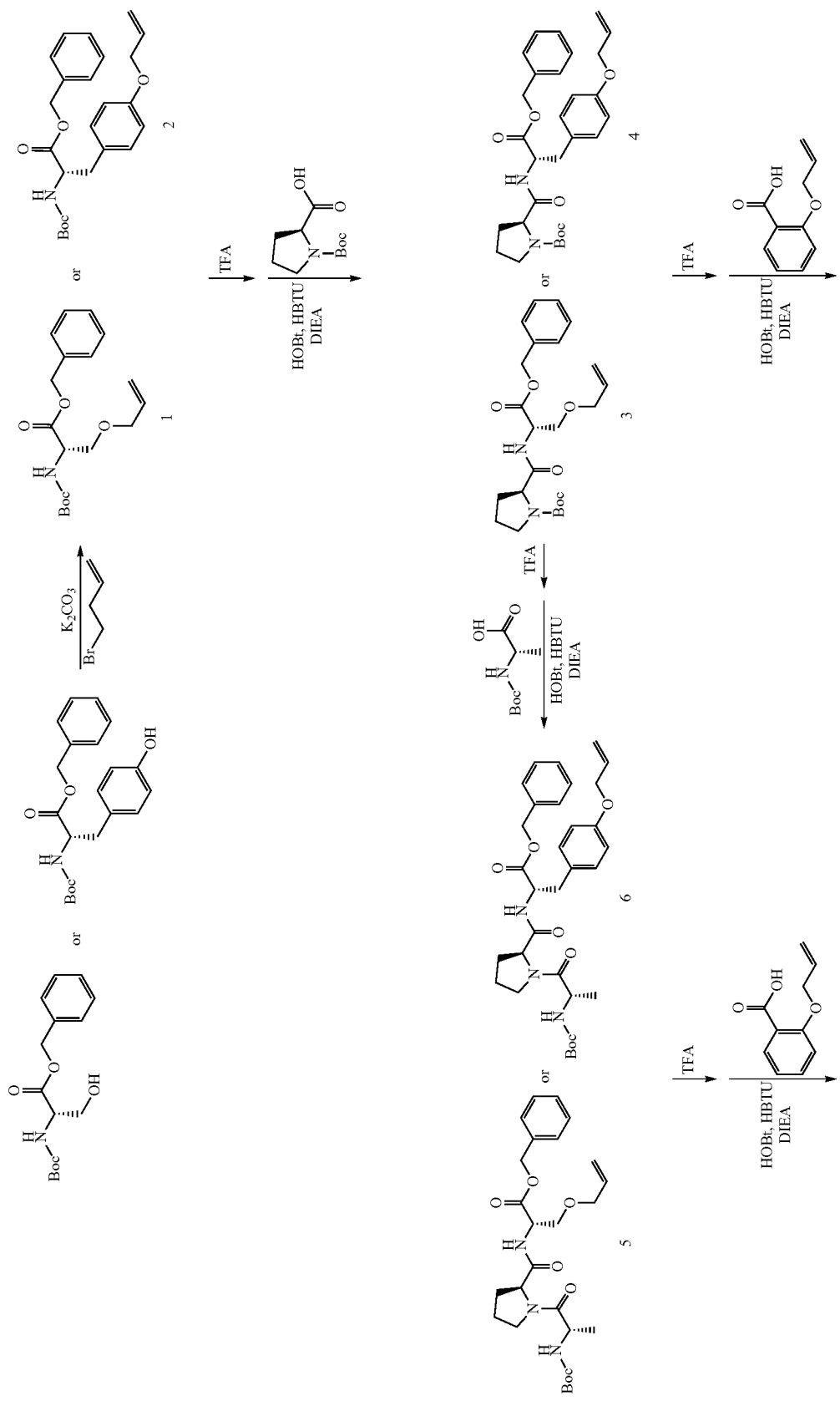

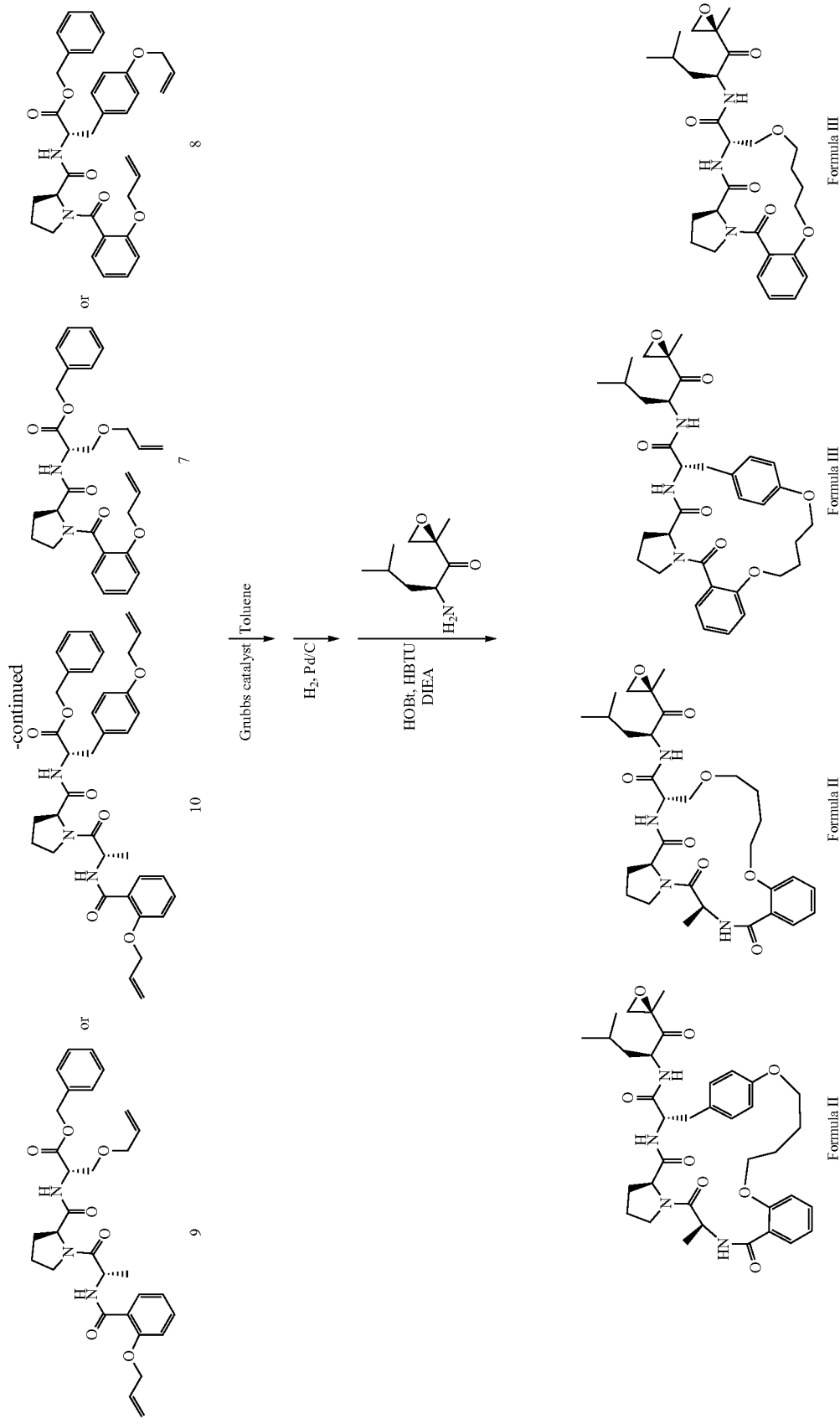

Commercially available Boc-protected serine or tyrosine were coupled with allyl bromide to furnished coupled products 1 and 2. Coupling of 1 and 2 with Boc-Pro using coupling agents HOBt and HBTU in the presence of diisopropyl ethylamine (DIEA) yielded dipeptides 3 and 4. TFA-catalyzed deprotection of Boc followed by a coupling reaction with Boc-Ala provided tripeptides 5 and 6. Removal of Boc from peptide intermediates (3, 4, 5, 6) in the presence of TFA and subsequent coupling with allylic benzoic acid furnished the left hand fragments of formula II and III (7, 8, 9 and 10). Macrocylization in the presence of Grubbs catalyst was performed, followed by hydrogenation and coupling with NH2-Leu-epoxide to provide the macrocyclic peptide epoxyketones (Formula II and III).

Example 3: Synthesis of Formula IV compound.

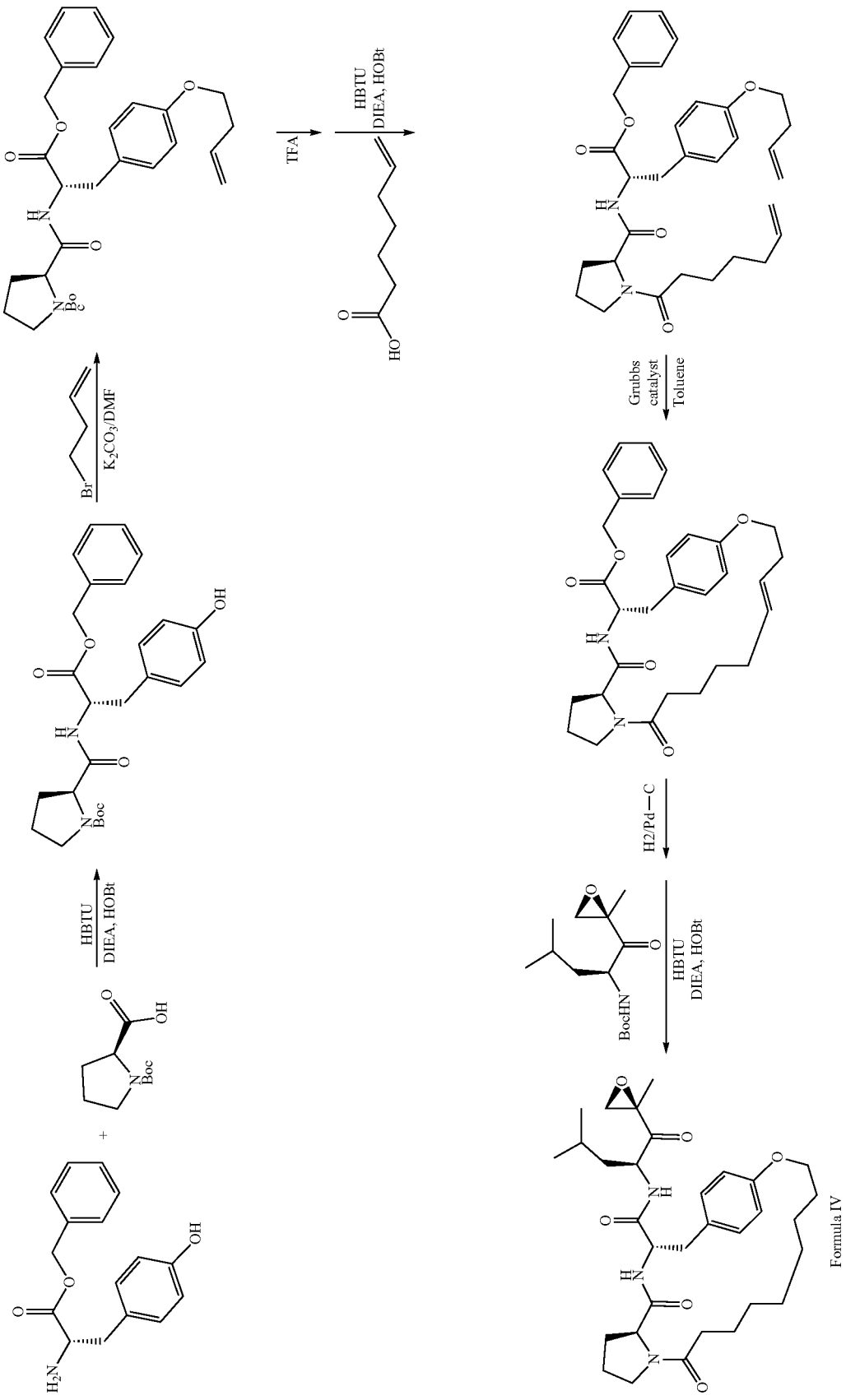

Example 4: Disclosed herein are a group of proteasome-inhibiting peptide epoxyketone compositions, including proteasome subunit LMP2 inhibitors and general proteasome inhibitors. In addition to their unique scaffold, the compounds show effectiveness in models of proteasome inhibitor resistance. This is notable, as MM patients who are initially responsive to currently FDA-approved proteasome inhibitors almost inevitably develop resistance to those drugs. Therefore, unique compounds provide an opportunity for an additional option for these refractory MM patients. Multiple clinical trials clearly demonstrated that the clinically approved proteasome inhibitors carfilzomib and bortezomib lack utility in the treatment of solid tumors due to their rapid metabolism, irreversible inhibition, sensitivity to resistance, and dose-limiting toxicities.[18,20,22,41,42]

The immunoproteasome is an inducible proteasome variant containing immuno-subunits low-molecular mass polypeptide-7 (LMP7), LMP2 and multicatalytic endopeptidase complex-1 (MECL-1) in place of constitutive counterparts X, Y and Z, respectively. While previous studies have found that the immunoproteasome is up-regulated in the brains of Alzheimer's disease (AD) patients, the exact role of the immunoproteasome in AD remains poorly defined. As disclosed herein, the impacts of LMP2 inhibition are characterized on progressive memory and learning impairments caused by amyloid-β (Aβ) deposition or lipopolysaccharide (LPS)-induced neuroinflammation in mouse models. Selective LMP2 inhibitors reversed disease progression independent of Aβ deposition or microglia activation. Data from these studies indicate that selective inhibition of LMP2 suppresses NLRP3 inflammasome-mediated neuroinflammation (neurotrauma) to improve the pathophysiology of neurodegenerative conditions in animal models. The impacts of LMP2 inhibition on progressive memory and learning impairments caused by amyloid-β (Aβ) deposition or lipopolysaccharide (LPS)-induced neuroinflammation was further explored in mouse models. Selective LMP2 inhibitors reversed disease progression independent of Aβ deposition and tau aggregation. Data from the studies indicate that selective inhibition of LMP2 suppresses cytokine production such as IL-6 and ameliorates neurodegenerative phenotypes in animal models. Overall, these findings suggest a role for LMP2 in the regulation of neuroinflammation and support that inhibition of LMP2 may offer a unique strategy for neurodegenerative diseases such as AD and AMD.

Example 5: With reference to FIGS. 1A-1D, inhibition of LMP2 was shown to improve cognitive impairment in an amyloid precursor protein (APP) transgenic mouse model of AD (Tg2576). FIG. 1A includes a schematic illustration showing the experimental schedule for a behavior test to assess cognitive impairment following administration of YU102 or YU102 epimer, as compared to control. YU102 is an inhibitor of the immunoproteasome subunit LMP2.

Figure 1B:
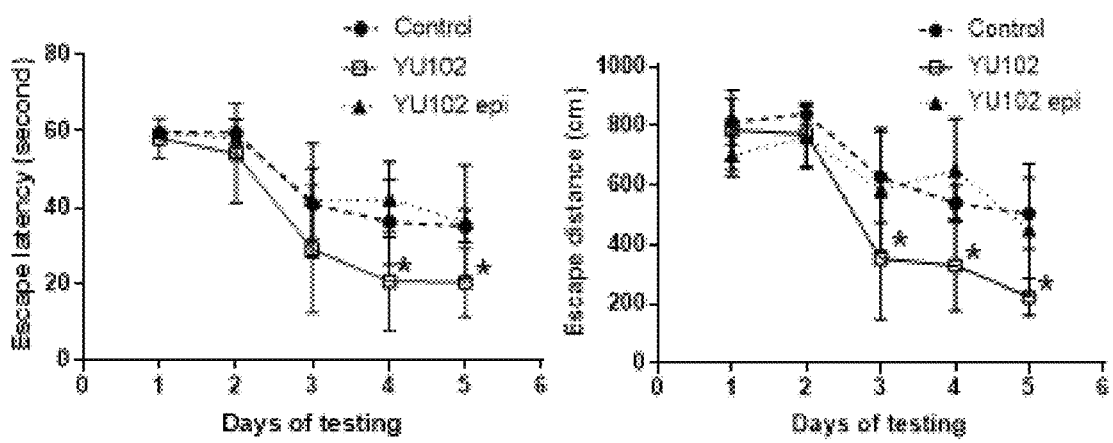

With reference to FIG. 1B, cognitive function in Tg2576 mice was evaluated by the Morris water maze test, and escape latency time (left) and escape distance of the mice (right) was assessed. Statistical analyses of escape latency and escape distance were performed via two-way ANOVA. The difference in escape latency on days 4-5 or distance on days 3-5 between control and YU102-treated mice was statistically significant (p-value<0.05, n=8), showing that inhibition of LMP2 ameliorates cognitive deficits in Tg2576 mice.

Figure 1C:
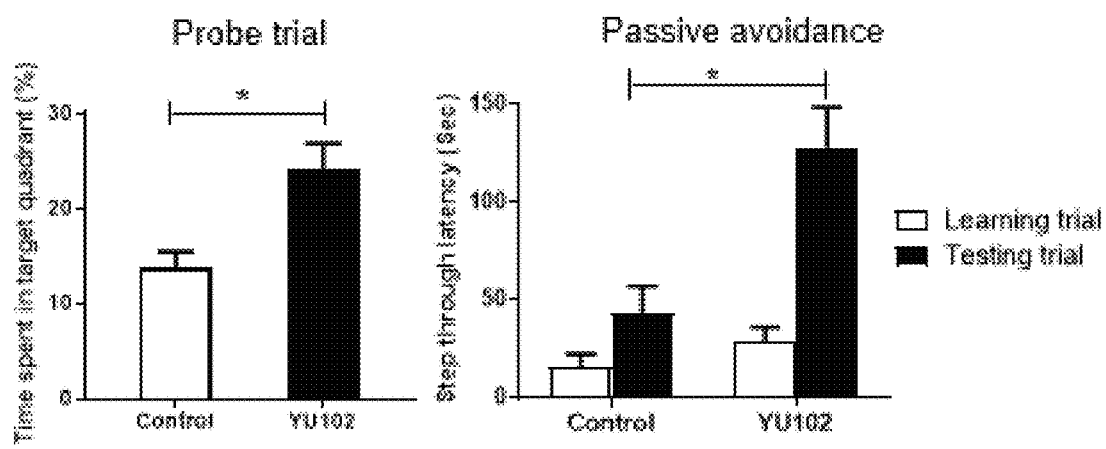

With reference to FIG. 1C, upon the completion of the Morris water maze test, Tg2576 mice were evaluated in the probe trial (left) and passive avoidance test (right). Statistical analyses of probe trial and passive avoidance were performed via Student's t-test. Differences in time spent in target quadrant or step through latency between control and YU102-treated mice were statistically significant (p-value<0.05, n=8), further illustrating that inhibition of LMP2 ameliorates cognitive deficits in Tg2576 mice.

Figure 1D:
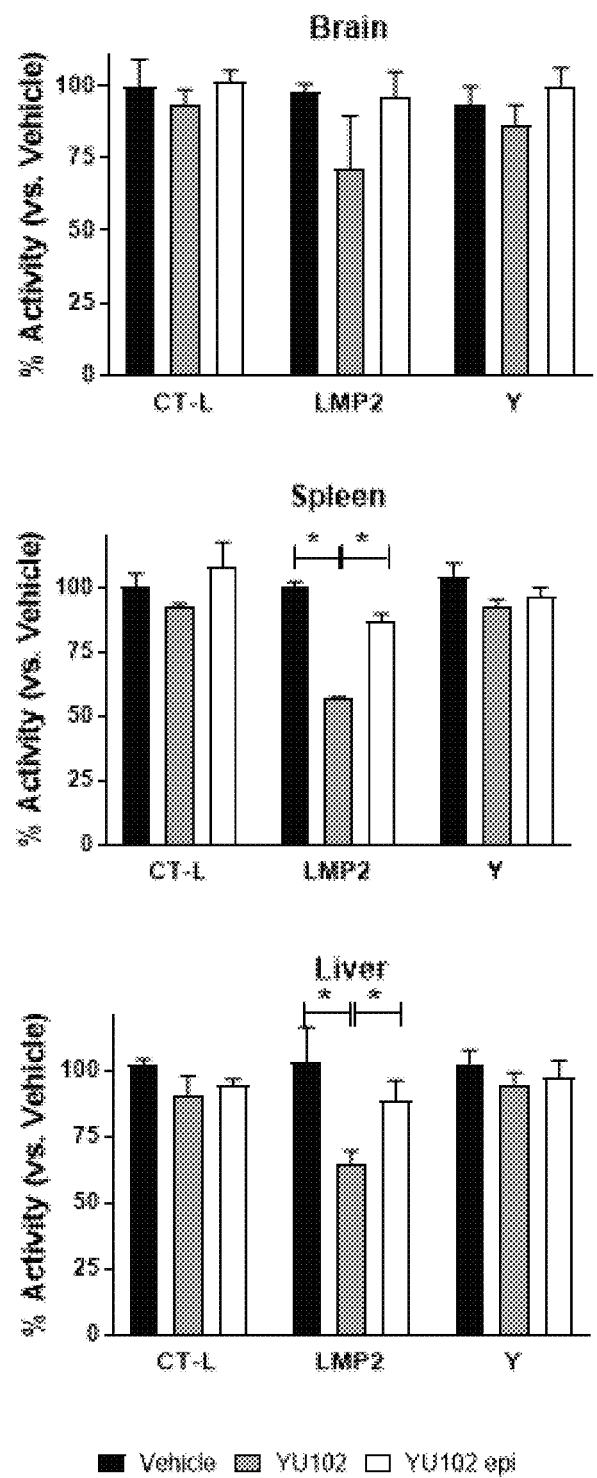

With reference to FIG. 1D, proteasome activities in brain, spleen, and liver tissue collected from mice treated with vehicle (control), YU102 (10 mg/kg), or YU102 epimer (10 mg/kg) were measured using fluorogenic substrates. Differences in LMP2 inhibitory activity in spleen and liver tissues between control and YU102-treated group or YU102-treated and YU102 epi-treated group were statistically significant (p-value<0.05, n=3), illustrating the systemic and selective inhibition of LMP2 in Tg2576 by YU102.

Figure 2:
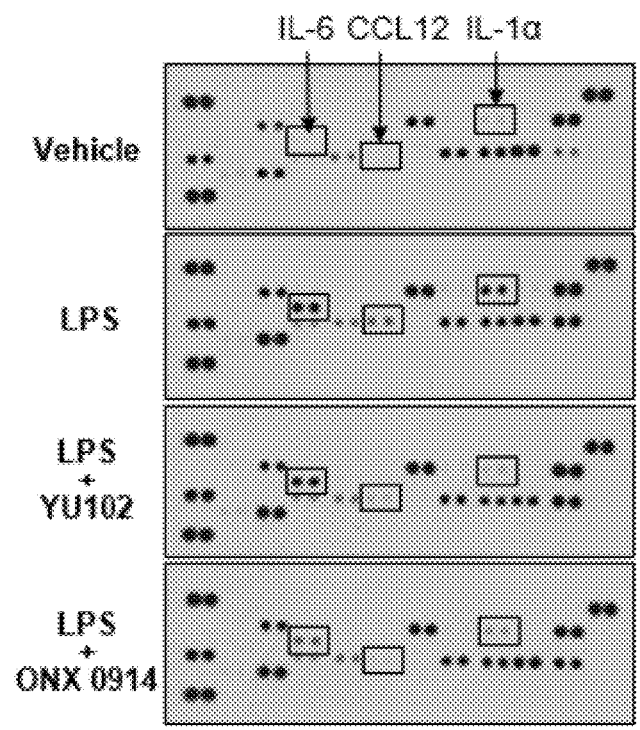
FIG. 2 illustrates the suppression of cytokine production by YU102 in LPS-stimulated BV-2 cells.
Figure 2:
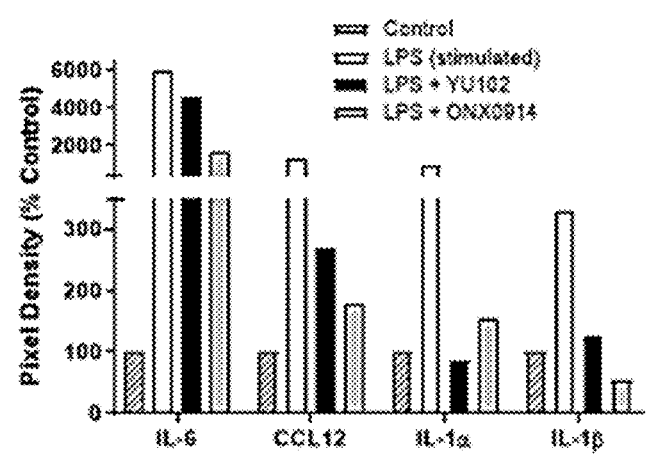

With reference to FIG. 2, cytokine production was assessed in LPS-stimulated BV-2 cells. Cytokine and chemokine protein array blots were obtained from BV-2 cells treated with vehicle, LPS (1 μg/mL) alone, and YU102 (3 μM) or ONX0914 (3 μM) with LPS (1 μg/mL). The signal intensity of each cytokine or chemokine was expressed relative to the mean of the intensity of the corresponding spots from vehicle control sample. The bar graph depicts the fold change of each cytokine or chemokine (mean). The arrow labels on the blot indicate cytokines that are most significantly impacted by YU102. These results illustrate suppression of cytokine production by YU102 in LPS-stimulated BV-2 cells.

Figure 3:
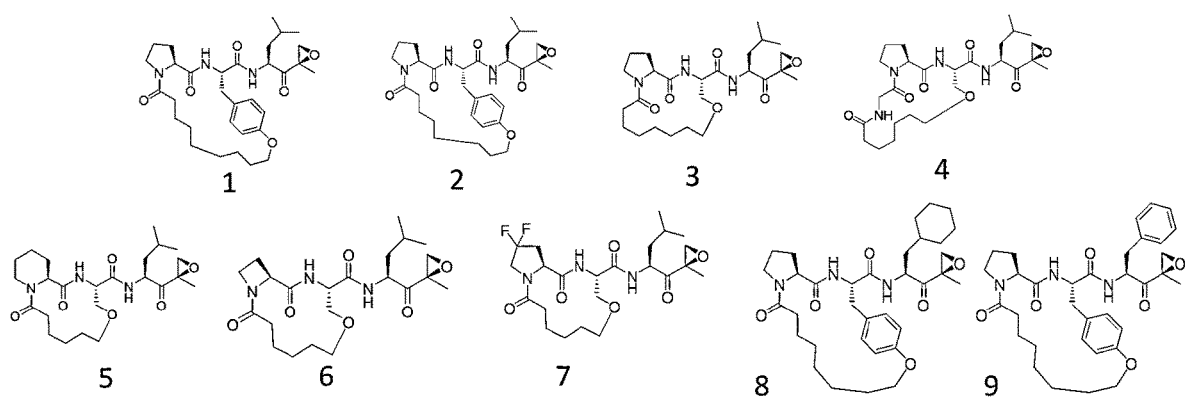
FIG. 3 includes the results of LMP2 inhibition by macrocyclic peptide epoxyketone compounds tested in triplicate against crude proteasomes isolated from RPMI 8266 cells with 100 μM Ac-nLPnLD-AMC and 100 μM Ac-PAL-AMC as substrates, respectively.

With reference to FIG. 3, the proteasome inhibitory activity of multiple macrocyclic peptide epoxyketones was assessed against crude proteasomes isolated from RPMI 8266 cells.

All publications, patents, and patent applications mentioned in this specification are herein incorporated by reference to the same extent as if each individual publication, patent, or patent application was specifically and individually indicated to be incorporated by reference, including the references set forth in the following list:

Reference

1. Muchamuel, T.; Basler, M.; Aujay, M. A.; Suzuki, E.; Kalim, K. W.; Lauer, C.; Sylvain, C.; Ring, E. R.; Shields, J.; Jiang, J.; Shwonek, P.; Parlati, F.; Demo, S. D.; Bennett, M. K.; Kirk, C. J.; Groettrup, M. A selective inhibitor of the immunoproteasome subunit LMP7 blocks cytokine production and attenuates progression of experimental arthritis. Nat Med 2009, 15, (7), 781-7.
2. Chen, X.; Zhang, X.; Wang, Y.; Lei, H.; Su, H.; Zeng, J.; Pei, Z.; Huang, R. Inhibition of immunoproteasome reduces infarction volume and attenuates inflammatory reaction in a rat model of ischemic stroke. Cell Death Dis 2015, 6, e1626.
3. Johnson, H. W. B.; Anderl, J. L.; Bradley, E. K.; Bui, J.; Jones, J.; Arastu-Kapur, S.; Kelly, L. M.; Lowe, E.; Moebius, D. C.; Muchamuel, T.; Kirk, C.; Wang, Z.; McMinn, D. Discovery of Highly Selective Inhibitors of the Immunoproteasome Low Molecular Mass Polypeptide 2 (LMP2) Subunit. ACS Med Chem Lett 2017, 8, (4), 413-417.
4. Jang, E. R.; Lee, N. R.; Han, S.; Wu, Y.; Sharma, L. K.; Carmony, K. C.; Marks, J.; Lee, D. M.; Ban, J. O.; Wehenkel, M.; Hong, J. T.; Kim, K. B.; Lee, W. Revisiting the role of the immunoproteasome in the activation of the canonical NF-kappaB pathway. Mol Biosyst 2012, 8, (9), 2295-302.

5. Keller, J. N.; Hanni, K. B.; Markesbery, W. R. Impaired proteasome function in Alzheimer's disease. J Neurochem 2000, 75, (1), 436-9.
6. Oh, S.; Hong, H. S.; Hwang, E.; Sim, H. J.; Lee, W.; Shin, S. J.; Mook-Jung, I. Amyloid peptide attenuates the proteasome activity in neuronal cells. Mech Ageing Dev 2005, 126, (12), 1292-9.
7. Tseng, B. P.; Green, K. N.; Chan, J. L.; Blurton-Jones, M.; LaFerla, F. M. Abeta inhibits the proteasome and enhances amyloid and tau accumulation. Neurobiol Aging 2008, 29, (11), 1607-18.
8. Almeida, C. G.; Takahashi, R. H.; Gouras, G. K. Beta-amyloid accumulation impairs multivesicular body sorting by inhibiting the ubiquitin-proteasome system. J Neurosci 2006, 26, (16), 4277-88.
9. Morozov, A. V.; Kulikova, A. A.; Astakhova, T. M.; Mitkevich, V. A.; Burnysheva, K. M.; Adzhubei, A. A.; Erokhov, P. A.; Evgen'ev, M. B.; Sharova, N. P.; Karpov, V. L.; Makarov, A. A. Amyloid-beta Increases Activity of Proteasomes Capped with 19S and 11S Regulators. J Alzheimers Dis 2016, 54, (2), 763-76.
10. Myeku, N.; Clelland, C. L.; Emrani, S.; Kukushkin, N. V.; Yu, W. H.; Goldberg, A. L.; Duff, K. E. Tau-driven 26S proteasome impairment and cognitive dysfunction can be prevented early in disease by activating cAMP-PKA signaling. Nat Med 2016, 22, (1), 46-53.
11. One, M.; Kamphuis, W.; Dooves, S.; Kooijman, L.; Chan, E. T.; Kirk, C. J.; Dimayuga Smith, V.; Koot, S.; Mamber, C.; Jansen, A. H.; Ovaa, H.; Hol, E. M. Reactive glia show increased immunoproteasome activity in Alzheimer's disease. Brain 2013, 136, (Pt 5), 1415-31.
12. Moritz, K. E.; McCormack, N. M.; Abera, M. B.; Viollet, C.; Yauger, Y. J.; Sukumar, G.; Dalgard, C. L.; Burnett, B. G. The role of the immunoproteasome in interferon-gamma-mediated microglial activation. Scientific reports 2017, 7, (1), 9365.
13. Aso, E.; Lomoio, S.; Lopez-Gonzalez, I.; Joda, L.; Carmona, M.; Fernandez-Yague, N.; Moreno, J.; Juves, S.; Pujol, A.; Pamplona, R.; Portero-Otin, M.; Martin, V.; Diaz, M.; Ferrer, I. Amyloid generation and dysfunctional immunoproteasome activation with disease progression in animal model of familial Alzheimer's disease. Brain Pathol 2012, 22, (5), 636-53.
14. Wagner, L. K.; Gilling, K. E.; Schormann, E.; Kloetzel, P. M.; Heppner, F. L.; Kruger, E.; Prokop, S. Immunoproteasome deficiency alters microglial cytokine response and improves cognitive deficits in Alzheimer's disease-like APPPS1 mice. Acta Neuropathol Commun 2017, 5, (1), 52.
15. Mundt, S.; Engelhardt, B.; Kirk, C. J.; Groettrup, M.; Basler, M. Inhibition and deficiency of the immunoproteasome subunit LMP7 attenuates LCMV-induced meningitis. Eur J Immunol 2016, 46, (1), 104-13.
16. Mishto, M.; Raza, M. L.; de Biase, D.; Ravizza, T.; Vasuri, F.; Martucci, M.; Keller, C.; Bellavista, E.; Buchholz, T. J.; Kloetzel, P. M.; Pession, A.; Vezzani, A.; Heinemann, U. The immunoproteasome beta5i subunit is a key contributor to ictogenesis in a rat model of chronic epilepsy. Brain Behav Immun 2015, 49, 188-96.
17. Mishto, M.; Bellavista, E.; Santoro, A.; Stolzing, A.; Ligorio, C.; Nacmias, B.; Spazzafumo, L.; Chiappelli, M.; Licastro, F.; Sorbi, S.; Pession, A.; Ohm, T.; Grune, T.; Franceschi, C. Immunoproteasome and LMP2 polymorphism in aged and Alzheimer's disease brains. Neurobiol Aging 2006, 27, (1), 54-66.
18. Mishto, M.; Bonafe, M.; Salvioli, S.; Olivieri, F.; Franceschi, C. Age dependent impact of LMP polymorphisms on TNFalpha-induced apoptosis in human peripheral blood mononuclear cells. Exp Gerontol 2002, 37, (2-3), 301-8.
19. Sacks, C. A.; Avorn, J.; Kesselheim, A. S. N Engl J Med 2017, 376, 1706-1708. Cummings, J.; Lee, G.; Mortsdorf, T.; Ritter, A.; Zhong, K. Alzheimers Dement (N Y) 2017, 3, 367-384.
20. Wise, J. BMJ 2016, 354, i4474.
21. Rafii, M. S. Lancet 2016, 388, 2842-2844.
22. Seifert, U.; Bialy, L. P.; Ebstein, F.; Bech-Otschir, D.; Voigt, A.; Schroter, F.; Prozorovski, T.; Lange, N.; Steffen, J.; Rieger, M.; Kuckelkorn, U.; Aktas, O.; Kloetzel, P. M.; Kruger, E. Cell 2010, 142, 613-24.
23. Kincaid, E. Z.; Che, J. W.; York, I.; Escobar, H.; Reyes-Vargas, E.; Delgado, J. C.; Welsh, R. M.; Karow, M. L.; Murphy, A. J.; Valenzuela, D. M.; Yancopoulos, G. D.; Rock, K. L. Nat Immunol 2011, 13, 129-35.
24. Opitz, E.; Koch, A.; Klingel, K.; Schmidt, F.; Prokop, S.; Rahnefeld, A.; Sauter, M.; Heppner, F. L.; Volker, U.; Kandolf, R.; Kuckelkorn, U.; Stangl, K.; Kruger, E.; Kloetzel, P. M.; Voigt, A. PLoS Pathog 2011, 7, e1002233.
25. Muchamuel, T.; Basler, M.; Aujay, M. A.; Suzuki, E.; Kalim, K. W.; Lauer, C.; Sylvain, C.; Ring, E. R.; Shields, J.; Jiang, J.; Shwonek, P.; Parlati, F.; Demo, S. D.; Bennett, M. K.; Kirk, C. J.; Groettrup, M. Nat Med 2009, 15, 781-7.
26. Johnson, H. W. B.; Anderl, J. L.; Bradley, E. K.; Bui, J.; Jones, J.; Arastu-Kapur, S.; Kelly, L. M.; Lowe, E.; Moebius, D. C.; Muchamuel, T.; Kirk, C.; Wang, Z.; McMinn, D. ACS Med Chem Lett 2017, 8, 413-417.
27. Jang, E. R.; Lee, N. R.; Han, S.; Wu, Y.; Sharma, L. K.; Carmony, K. C.; Marks, J.; Lee, D. M.; Ban, J. O.; Wehenkel, M.; Hong, J. T.; Kim, K. B.; Lee, W. Mol Biosyst 2012, 8, 2295-302.
28. Keller, J. N.; Hanni, K. B.; Markesbery, W. R. J Neurochem 2000, 75, 436-9.
29. Oh, S.; Hong, H. S.; Hwang, E.; Sim, H. J.; Lee, W.; Shin, S. J.; Mook-Jung, I. Mech Ageing Dev 2005, 126, 1292-9.
30. Tseng, B. P.; Green, K. N.; Chan, J. L.; Blurton-Jones, M.; LaFerla, F. M. Neurobiol Aging 2008, 29, 1607-18.
31. Almeida, C. G.; Takahashi, R. H.; Gouras, G. K. J Neurosci 2006, 26, 4277-88.
32. Myeku, N.; Clelland, C. L.; Emrani, S.; Kukushkin, N. V.; Yu, W. H.; Goldberg, A. L.; Duff, K. E. Nat Med 2016, 22, 46-53.
33. Orre, M.; Kamphuis, W.; Dooves, S.; Kooijman, L.; Chan, E. T.; Kirk, C. J.; Dimayuga Smith, .; Koot, S.; Mamber, C.; Jansen, A. H.; Ovaa, H.; Hol, E. M. Brain 2013, 136, 1415-31.
34. Moritz, K. E.; McCormack, N. M.; Abera, M. B.; Viollet, C.; Yauger, Y. J.; Sukumar, G.; Dalgard, C. L.; Burnett, B. G. Scientific reports 2017, 7, 9365.
35. Mishto, M.; Bellavista, E.; Santoro, A.; Stolzing, A.; Ligorio, C.; Nacmias, B.; Spazzafumo, L.; Chiappelli, M.; Licastro, F.; Sorbi, S.; Pession, A.; Ohm, T.; Grune, T.; Franceschi, C. Neurobiol Aging 2006, 27, 54-66.
36. Nijholt, D. A.; de Graaf, T. R.; van Haastert, E. S.; Oliveira, A. O.; Berkers, C. R.; Zwart, R.; Ovaa, H.; Baas, F.; Hoozemans, J. J.; Scheper, W. Cell Death Differ 2011, 18, 1071-81.
37. Aso, E.; Lomoio, S.; Lopez-Gonzalez, I.; Joda, L.; Carmona, M.; Fernandez-Yague, N.; Moreno, J.; Juves, S.; Pujol, A.; Pamplona, R.; Portero-Otin, M.; Martin, V.; Diaz, M.; Ferrer, I. Brain Pathol 2012, 22, 636-53.
38. Wagner, L. K.; Gilling, K. E.; Schormann, E.; Kloetzel, P. M.; Heppner, F. L.; Kruger, E.; Prokop, S. Acta Neuropathol Commun 2017, 5, 52.
39. Ho, Y. K.; Bargagna-Mohan, P.; Mohan, R.; Kim, K. B. Chem Bio! 2007, 14, 419-430.
40. Mishto, M.; Bonafe, M.; Salvioli, S.; Olivieri, F.; Franceschi, C. Exp Gerontol 2002, 37, 301-8.
41. Tak, H.; Haque, M. M.; Kim, M. J.; Lee, J. H.; Baik, J. H.; Kim, Y.; Kim, D. J.; Grailhe, R.; Kim, Y. K. PLoS One 2013, 8, e81682.
42. Jiang, Z.; Georgel, P.; Du, X.; Shamel, L.; Sovath, S.; Mudd, S.; Huber, M.; Kalis, C.; Keck, S.; Galanos, C.; Freudenberg, M.; Beutler, B. Nat Immunol 2005, 6, 565-70.
43. Ratnayaka, J. A.; Serpell, L. C.; Lotery, A. J. Eye (Lond) 2015, 29, 1013-26.
44. Keenan, T. D.; Goldacre, R.; Goldacre, M. J. JAMA Ophthalmol 2014, 132, 63-8. Chiu, K.; Chan, T. F.; Wu, A.; Leung, I. Y.; So, K. F.; Chang, R. C. Age (Dordr) 2012, 34, 633-49.
45. Ding, J. D.; Lin, J.; Mace, B. E.; Herrmann, R.; Sullivan, P.; Bowes Rickman, C. Vision Res 2008, 48, 339-45.
46. Voorhees, C. V.; Williams, M. T. Nat Protoc 2006, 1, 848-58.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

Finally, for further explanation of the features, benefits and advantages of the present invention, attached hereto is an Appendix, which is incorporated herein by this reference.

As such, the following are representitive claims:

1. A method of treating Alzheimer's disease in a subject, comprising: administering to the subject an effective amount of a pharmaceutical composition containing a compound, a pharmaceutically acceptable salt, or a solvate thereof, of the formula:

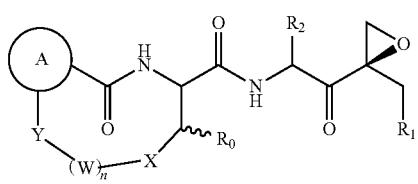

wherein
(a) X and Y are independently selected from the group consisting of —$CH_2$—, —$CH_2CH_2$—, —O—, —$CH_2O$—, —NH—, —$CH_2NH$—, —N($CH_3$)—, —$CH_2N(CH_3)$—, —C(=O)—, —$CH_2C(=O)$—, —$C_6H_4$—, —$CH_2$—($C_6H_4$)—, —($C_6H_4$)-$F_{1-4}$-, —$CH_2$—$C_6H_4$-(F)$_{1-4}$-, -pyrazole-, -imidazole-, -thiazole-, -oxazole-, -morpholine-, -pyridine-, -piperazine-, and -pyrrole-;
(b) W is —$CH_2$—, —$CH_2OCH_2$—, —$CH_2CH_2O$—, or —$CH_2CH_2OCH_2CH_2$—;
(c) n is 1, 2, 3, 4, 5, 6, 7, or 8;
(d) $R_0$ is H, OH, F, $CH_3$, or $OCH_3$;
(e) $R_1$ is selected from the group consisting of:
(i)

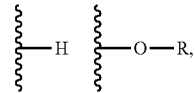

wherein R is H, $CH_3$, isopropyl, t-butyl, methoxymethyl (MOM), menthoxyethoxy methyl (MEM), or $(CH_2)nCH_3$ wherein n is 1, 2, or 3;
(ii)

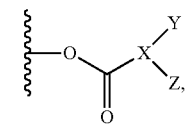

wherein X, Y, and Z are independently selected from the group consisting of H, CH, N, $CH_3$, and $CH_2CH_3$;
(iii)

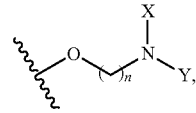

wherein X and Y are independently selected from the group consisting of H, $CH_3$, and $(CH_2)nCH_3$ wherein n is 1, 2, or 3;
(iv)

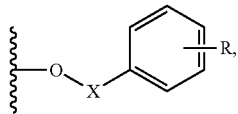

wherein X is $CH_2$ or C=O; and R is H, $CH_3$, $N(CH_3)_2$, or Fn, wherein n is 0, 1, 2, 3, 4, or 5;
(v)

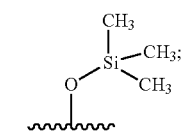

(vi)

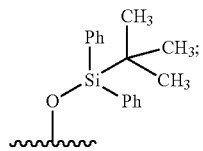

(v)

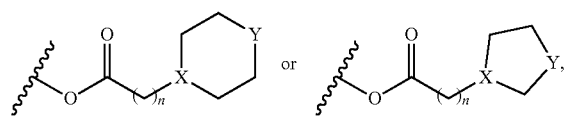

wherein X is CH or N; Y is $CH_2$, O, or N-R, wherein R is H, $CH_3$ or $COCH_3$; and n is 0, 1, or 2;

(vi)

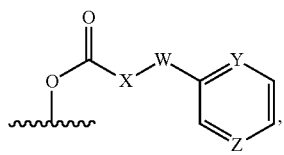

wherein X, Y, and Z are independently selected from the group consisting of CH, $CH_2$, N, NH, and O; and W is $CH_2$ or $CH_2CH_2$;

(vii)

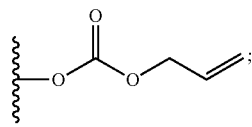

(viii)

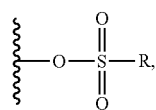

wherein R is $CH_3$, $CH_2CH_2Ph$-Fn, or $CH_2PhFn$, wherein n is 0, 1, 2, 3, 4, or 5;

(ix)

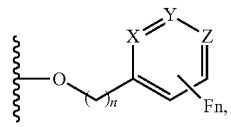

wherein X, Y, and Z are independently selected from N and CH, and n is 0, 1, 2, or 3;
(f) $R_2$, $R_3$ and $R_4$ are independently selected from the group consisting of:
(i) Gly, Ala, Pro, Leu, Ile, Phe, Tyr, Val, Ser, methyl-oxySerine, homoPhe, norVal, or norLeu;
(ii)

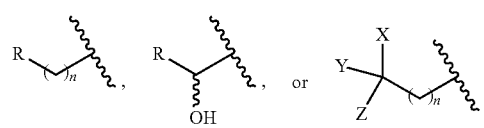

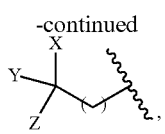

wherein X and Y are independently selected from the group consisting of H, $CH_3$, and $CH_2CH_3$; R and Z are independently selected from the group consisting of H, OH, $OCH_3$, $OCH_2CH_3$, Ph, and OPh; and n is 1, 2, or 3;

(iii)

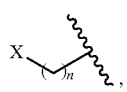

wherein X is cyclopropyl, cyclopentyl, or cyclohexyl, and n is 1, 2, or 3;

(iv)

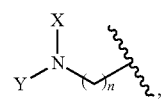

wherein X and Y are independently selected from the group consisting of H, $CH_3$, $CO(CH_3)$, and $CO2Bzl$, and n is 1, 2, or 3;

(v)

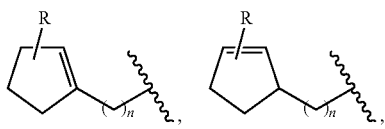

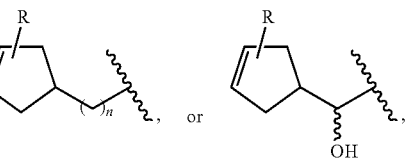

wherein R is H, $CH_3$, or $(F)_{1-3}$, and n is 1, 2, or 3;

(vi)

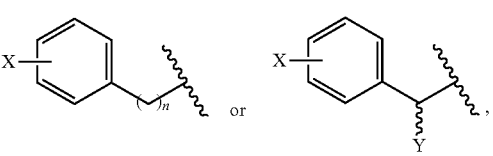

wherein X and Y are independently selected from the group consisting of H, Fn, Cl, $CH_3$, $OCH_3$, $OHCOCH_3$, $NH_2$, $NH(CH_3)$ and NHFmoc, and n is 1, 2, or 3;

(vii)

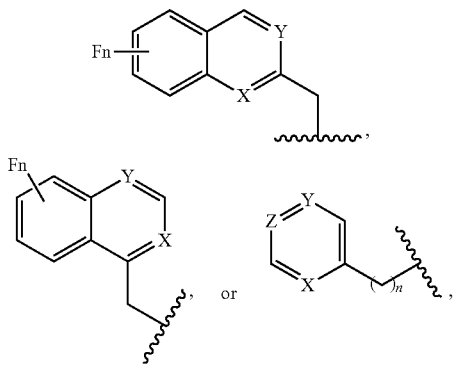

wherein X, Y, and Z are independently selected from CH and N, and n is 1, 2, or 3;

(viii)

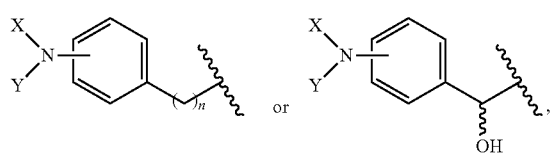

wherein X and Y are independently selected from the group consisting of H, CH₃, and COCH₃, and n is 1, 2, 3, or 4;

(ix)

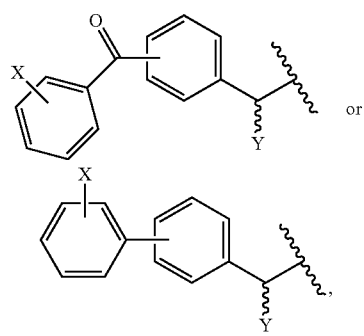

wherein X is H, Fn, CH₃, or OCH₃; Y is H or OH, and n is 1, 2, 3, 4, or 5;

(x)

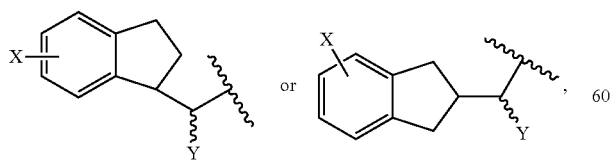

wherein X and Y are independently selected from the group consisting of H, Fn, CH₃ OCH₃, OH, COCH₃; and n is 1, 2, 3, 4, or 5;

(xi)

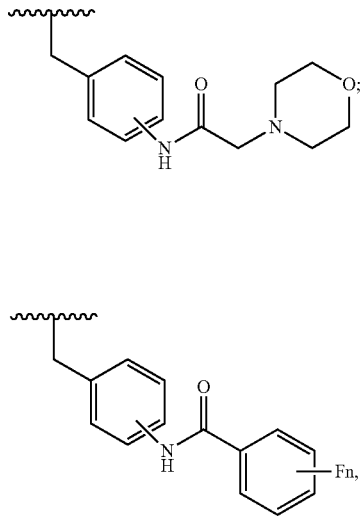

(xii)

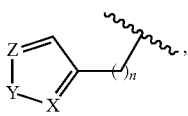

wherein n is 0, 1, 2, 3, 4, or 5;

(xii)

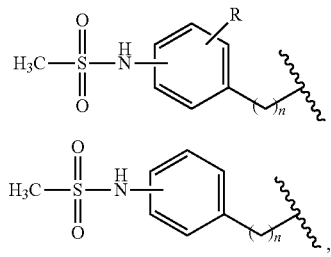

wherein X, Y, and Z are independently selected from the group consisting of CH, CH₂, N, NH, N(CH₃), and O, and n is 1, 2, or 3;

(xiv)

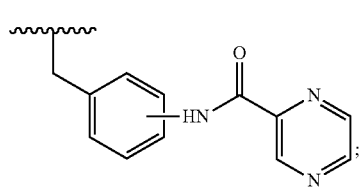

wherein R is H, CH₃, or Fn, wherein n is 0, 1, 2, or 3;

(xv)

and (xvi)

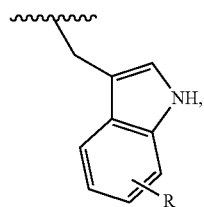

wherein R is H, Fn, or (CH₃)n; wherein n is 0, 1, 2, 3, or 4 and (g) A is selected from:
(i)

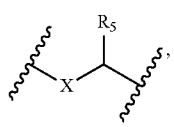

wherein
R₅ is selected from the group consisting of:
H, CH₃, (CH₂)₁₋₃CH₃, CH(CH₃)₂, CH₂CH(CH₃)₂, CH(CH₃)CH(CH₃)₂, CH₂OH, CH₂OCH₃, CH₂(C₆H₅), CH₂CH₂(C₆H₅), and CH₂(C₆H₄)—OH, and
X is selected from the group consisting of CH₂, NH, and N(CH₃);

(ii)

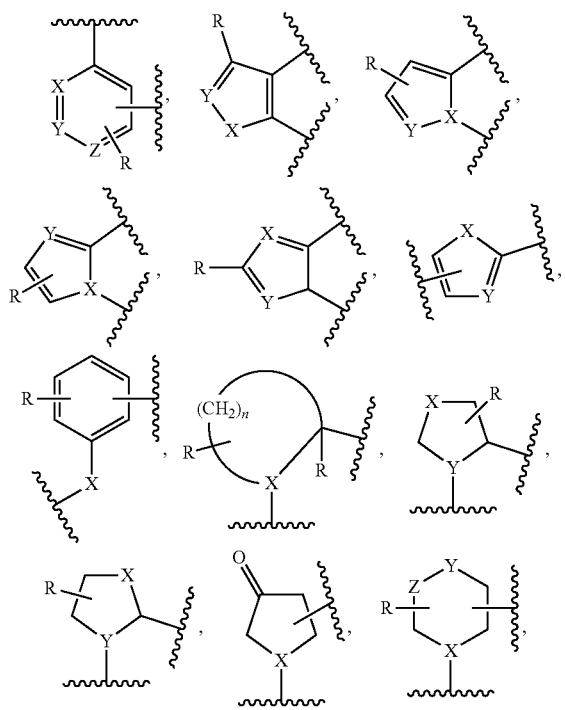

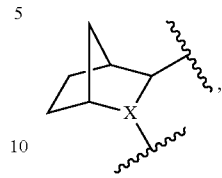

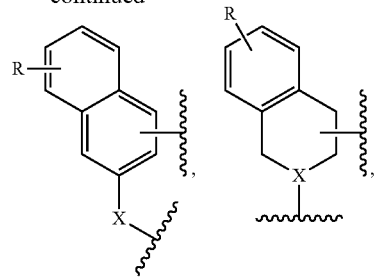

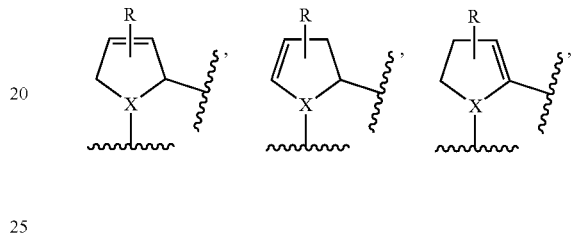

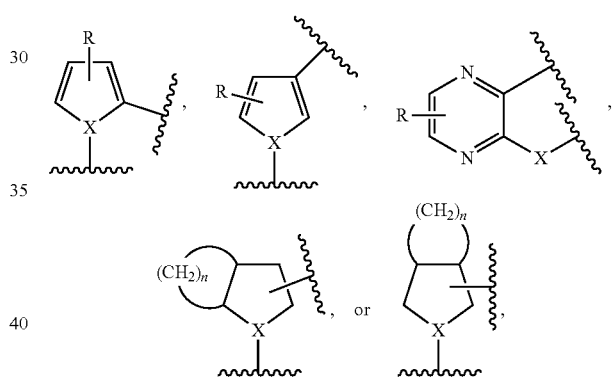

wherein X, Y, and Z are independently selected from the group consisting of CH, CH₂, C═O, N, NH, O, S, and N-R, R is H, OH, (F)₁₋₄, CH₃, OCH₃, CH₂OCH₃, NH₂, NH(CH₃), N(CH₃)₂, N(C═O)CH₃, phenyl, phenyl(F)₁₌₄, pyrazole, imidazole, thiazole, oxazole, morpholine, pyridine, piperazine, or pyrrole, and n is 2, 3, 4, or 5.

2. The method of claim 1, wherein the compound has a formula selected from the group consisting of:

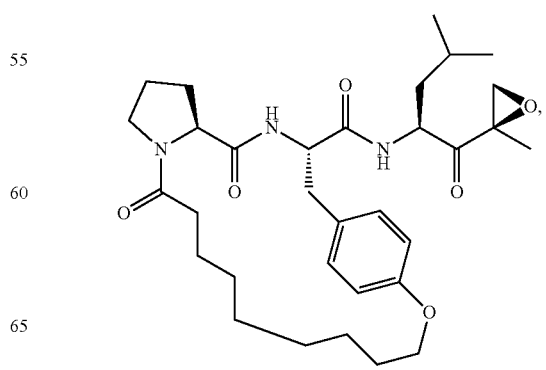

-continued
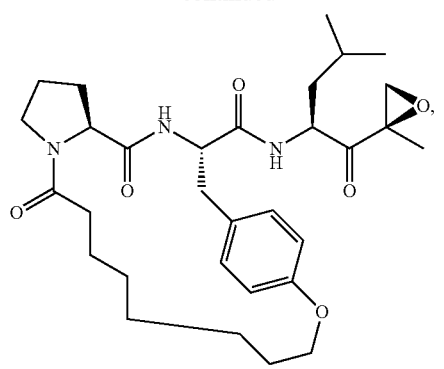
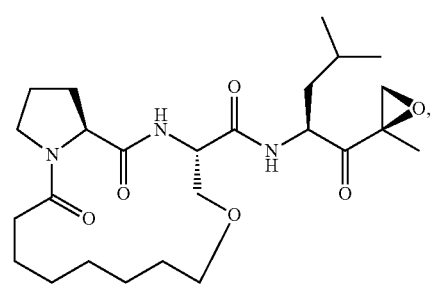
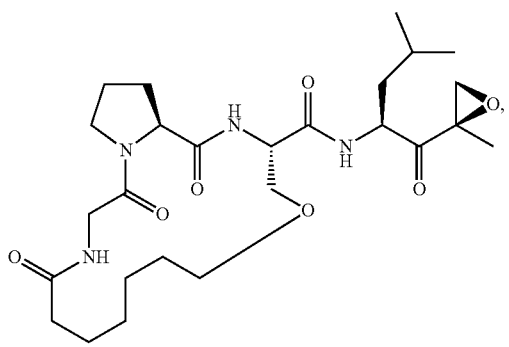
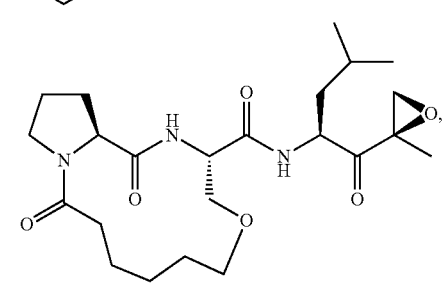
-continued
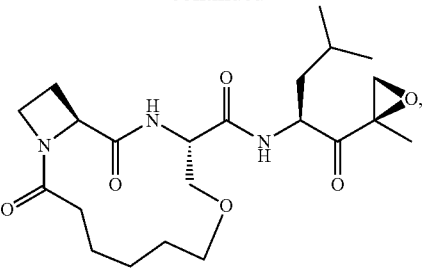
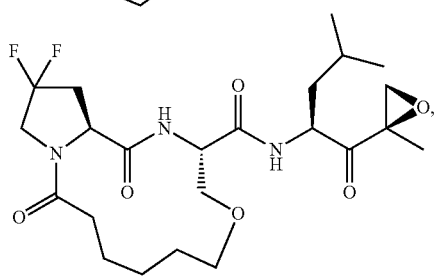
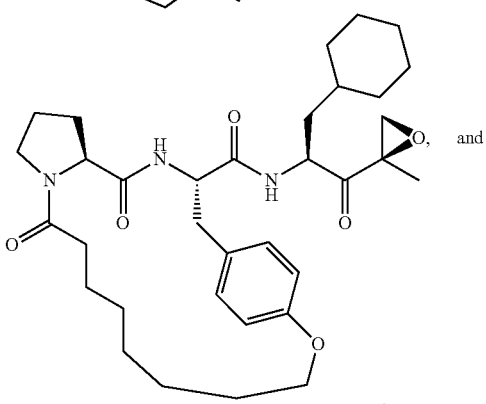
and
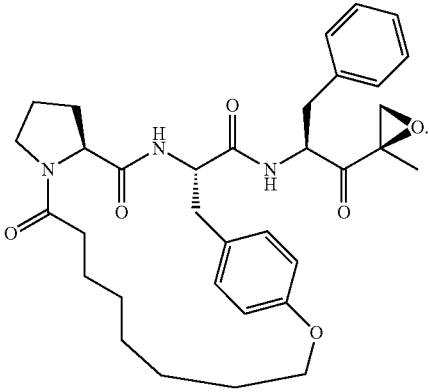
* * * * *